US006447822B1

(12) United States Patent
Ludovici et al.

(10) Patent No.: US 6,447,822 B1
(45) Date of Patent: Sep. 10, 2002

(54) METHOD FOR PREPARING AND USING B-STARCH

(75) Inventors: Karl Ludovici, Bergisch Gladbach (DE); Jan Buining, Aalden (NL)

(73) Assignees: Pfeifer & Langen, Cologne (DE); Dairy Products Supply, Emmen (NL)

( * ) Notice: Subject to any disclaimer, the term of this patent is extended or adjusted under 35 U.S.C. 154(b) by 0 days.

(21) Appl. No.: 09/646,103

(22) PCT Filed: Mar. 18, 1999

(86) PCT No.: PCT/EP99/01812

§ 371 (c)(1),
(2), (4) Date: Sep. 21, 2000

(87) PCT Pub. No.: WO99/48383

PCT Pub. Date: Sep. 30, 1999

(30) Foreign Application Priority Data

Mar. 21, 1998 (DE) .......................................... 198 12 511

(51) Int. Cl.⁷ ................................................. A21D 2/00
(52) U.S. Cl. ....................................................... 426/18
(58) Field of Search ............................... 426/18, 48, 49, 426/52, 549, 658, 661, 19, 20

(56) References Cited

FOREIGN PATENT DOCUMENTS

| EP | 0 231 729 | 8/1987 |
|----|-----------|--------|
| GB | 465884    | 5/1937 |

*Primary Examiner*—Leslie Wong
(74) *Attorney, Agent, or Firm*—Jacobson Holman, PLLC

(57) ABSTRACT

The process for the enzymatic processing of the third phase of dough separation containing both B-starch and the soluble flour components is effected by adding, after the usual mechanical separation of A starch and gluten, amylases and hemicellulases to the third phase of dough separation, immediately heating at temperatures of from 55 to 75° C., preferably 60 to 70° C., and immediately concentrating by evaporation following saccharification and pentosane partial hydrolysis. The thus obtained product can be advantageously employed as a partial or complete substitute of dairy raw materials or vegetable carbohydrates in animal feeds, food products and ices.

10 Claims, No Drawings

METHOD FOR PREPARING AND USING B-STARCH

B-starch is produced in substantial amounts in the conventional flour processing in starch and glucose factories by mixing the flour with water to give a dough having from 25% to 40% of dry substance and separating it to its components by centrifugation after a maturing period; cf. G. Tegge, "Stärke und Stärkederivate", Behr Verlag (publishers), 1984.

The phase of the dough having the highest specific gravity, the so-called A-starch, can be separated from the dough by decantation, purified from fiber fragments in rotary screens, and washed in hydrocyclones.

The gluten, which has a lower specific gravity, is obtained in an agglomerated form as a further phase of the dough and is separated from the dough after the separation of the A-starch, for example, by sieve bends, or even prior to the separation of the A-starch by decantation in extractors. The simultaneous separation of A-starch and gluten in three-phase decanters is also known.

In addition to the so-called B-starch, the third phase of the dough, after the separation of the A-starch and gluten, contains the soluble components of flour, namely albumins, globulins, pentosanes, ashes, soluble carbohydrates, etc. On a microscopical scale, B-starch consists of conglomerates of starch granules, which are mostly rather small, with proteins, hemicelluloses, fibers and the like. Therefore, as compared with A-starch, B-starch has a lower specific gravity.

To date, B starch has been processed in various ways. Thus, after dehydrating on cylinder dryers, it has often been processed into so-called swell-starch flour which is used as a feed component or as an inexpensive thickener. If the B-starch is dehydrated by centrifugation prior to drying, the soluble components of the flour are lost with the waste-water stream.

Another possibility for utilizing B-starch is the complete enzymatic saccharification of the starch fractions obtained to yield glucose, followed by concentration by evaporation. In this process, the Maillard reaction gives rise to dark-brown colored syrups, which are in turn suitable as raw materials for a wide variety of fermentation methods or as binders. One possibility for this digestion is direct fermentation into alcohol.

It has also been tried to treat B-starch enzymatically or chemically in such a way that as pure as possible a starch fraction can be separated. Thus, for example, part of the B-Starch conglomerates are cleaved by hemicelluloses, proteinases or aqueous sodium hydroxide, so that pure starch granules are released, and the viscosity of the third phase of dough separation is reduced. Due to their higher specific gravity and the reduced viscosity in their environment, the starch granules can in turn be separated by centrifugation. Due to its relatively high purity, the starch fraction thus obtained can be combined with A-starch for certain processing applications. Thus, the yield of A-starch is increased. The minor contaminants present in the additional starch thus produced do not affect the further processing into glucose syrup, for example, or do so but slightly, for example, by resulting in an increased refining expenditure.

One drawback of these methods is the substantial devaluation of the non-starch fraction of the third phase of dough separation. Products are obtained which have a bad taste and are so rich in ashes that they can only be mixed into pig food or dried onto fodder bran. Thus, a drawback of all methods known to date is that substantial fractions of per se valuable components are obtained in a minor quality and actually cannot be utilized, but must be disposed of.

Thus, it has been the object of the invention to provide a process for the enzymatic processing of the third phase of dough separation in which all components of the third phase of dough separation, if possible, are obtained in a high quality and are therefore well utilizable, so that they are obtained in an economically and ecologically valuable form and need no longer be disposed of.

This object is achieved by adding, after the usual mechanical separation of A starch and gluten, amylases and hemicellulases to the third phase of dough separation containing B-starch and the soluble flour components, immediately heating it at temperatures of from 55 to 75° C., preferably 60 to 70° C., and immediately concentrating it by evaporation following saccharification and pentosane partial hydrolysis.

Preferably, the method is performed by selecting the quantities of the added enzymes and the reaction conditions to obtain a balanced ratio of glucose, dextrines and residual starch.

Further, the reaction conditions are selected such that the Maillard reaction occurs as little as possible or not at all.

Finally, the reaction conditions will preferably be selected such that the soluble proteins of the third phase of dough separation are not altered and that as little as possible microbial fermentation occurs.

The process products thus obtained can be used as a partial or complete substitute of raw materials made from skimmed milk or vegetable carbohydrates in animal feeds, especially in feeds for young animals, and in food products, especially in spray-dried products, sweets or ices.

For performing the process according to the invention, amylases and hemicellulases are added to the third phase of dough separation containing both B-starch and the soluble flour components as soon as possible after decantation, immediately followed by heating at temperatures of from 55 to 75° C., preferably from 60 to 70° C. Optionally, the pH value may be adjusted prior to the addition of the amylases and hemicellulases or prior to heating, in order to, on the one hand, accelerate the digestion of the B-starch by the amylases and hemicellulases and, on the other hand, suppress microbial fermentation as much as possible. Further, the process conditions are preferably selected such that the Maillard reaction occurs as little as possible. It is also possible to leave the soluble proteins of the third phase of dough separation unaltered and thus preserve them as valuable components.

The heating of the reaction mixture can be effected either discontinuously in a stirred tank or continuously with live steam in a starch liquefying jet with a downstream tubular reactor, dwelling times of from 1 to 1.5 hours having proven sufficient and optimum. Both process variants allow for an exact control of dwelling time to ensure controlled saccharification. Optimum properties of the products prepared according to the invention are obtained when a balanced ratio of glucose to dextrines is achieved. Too high glucose proportions cause a strong formation of color and taste by the Maillard reaction in the subsequent evaporation step. Further, the free glucose causes a decrease of amino acids by the Maillard reaction. Too high a proportion of dextrines is undesirable, on the other hand, since the digestive system of young calves, for example, contains virtually no amylase. Further, a high proportion of dextrines adversely affects evaporation by an increased viscosity and formation of a film.

After the heating according to the invention, the product is evaporated, preferably carefully, or spray-dried to a content of from 30% to 50% by weight of dry substance. Temperatures of more than 72° C. have to be avoided in this process too, in order to suppress the denaturation of soluble proteins. Short dwelling times at high temperatures suppress brown discoloration by the Maillard reaction. By extreme hygiene, in particular, a microbiological contamination and thus an undesirable degradation of the valuable soluble proteins of the third phase of dough separation and contamination with microbial metabolites can be prevented.

The products prepared according to the invention are free from lactose and can therefore be used in animal feeds which are supposed to contain little or no lactose. Depending on the process conditions, the products contain from 2% to 10% by weight of monosaccharides, from 25% to 50% by weight of disaccharides, from 2% to 10% by weight of trisaccharides and minor amounts of between 0 and 4% of longer-chain oligosaccharides.

The products prepared according to the invention can be used, for example, in animal feeds and especially in feeds for young animals, in part as a substitute of products from the dairy industry or of protein sources of vegetable origin. Thus, desugarized whey which is rich in ashes but poor in carbohydrates is obtained in the industry.

According to the invention, products poor in ashes and rich in carbohydrates containing valuable protein components are produced. Mixtures of these two products are excellently useful for the fattening of calves. Thus, such mixtures can be employed instead of skimmed milk powder. While the dairy products generally contain from 6.5% to 20% by weight of minerals, the products prepared according to the invention contain from 1% to 5% by weight of minerals, based on the dry substance. Their protein content is between 7 and 35%, and the nutritive value of these proteins is preserved because they are maintained in a native condition, if possible. The smell, taste and color of the animal feeds thus obtained meet the highest demands.

Further, the products prepared according to the invention are suitable for the partial or complete substitution of dairy raw materials in foods, especially in spray-dried products and sweets. Thus, for example, part of the relatively expensive skimmed milk powder is ices can be replaced, reducing the lactose content into the bargain. The tendency to crystallize is reduced thereby so that the ices are softer. The products prepared according to the invention are also very useful for the preparation of caramel, for the filling of chocolate bars etc. in which demineralized whey is already used. The relatively high ashes content in whey adversely affects taste. Non-demineralized whey can be advantageously employed in admixture with the products prepared according to the invention. If desired, the quality of the products can be further improved by adding emulsifiers and fats, in which case the good properties are also maintained and products are obtained which can be considered having a very high quality with respect to taste, smell and color. This also applies to feeds for other animals, such as lambs, dogs, cats and even fish.

We claim:

1. A process for the enzymatic processing of the third phase of dough separation containing B-starch and soluble flour components, characterized in that, after mechanical separation of A-starch and gluten, amylases and hemicellulases are added to the third phase of dough separation, the phase is immediately heated at temperatures of from 55 to 75° C., and inmmediately concentrated by evaporation following saccharification and pentosane partial hydrolysis.

2. The process according to claim 1, characterized in that the temperatures are from 60 to 70° C.

3. The process according to claim 1, characterized in that the phase is immediately heated at temperatures of from 60 to 70° C.

4. The process according to claim 1, characterized in that the quantities of the added enzymes and the reaction conditions are selected to obtain a balanced ratio of glucose to dextrines.

5. The process according to claim 1, characterized in that the reaction conditions are selected such that the Maillard reaction occurs minimally.

6. The process according to claim 1, characterized in that the reaction conditions are selected such that the soluble proteins of the third phase of dough separation are altered minimally.

7. The process according to claim 1, characterized in that the reaction conditions are selected such that minimal microbial fermentation occurs.

8. The process according to claim 1, characterized in that the resulting product has the following composition, based on the dry substance:

lipids: from 1% to 5% by weight;

proteins: from 7% to 35% by weight (N×6.25);

carbohydrates: from 60 to 80% by weight;

minerals: from 1 to 5% by weight.

9. A method of using the enzymatically processed third phase of dough separation, prepared according to claim 1, comprising partially or completely substituting the enzymatically processed third phase of dough separation in place of dairy raw materials or vegetable carbohydrates in animal feeds and in food products.

10. The method of claim 9, characterized in that the food products are spray-dried products, sweets, and ices.

* * * * *